United States Patent
Hadba

(10) Patent No.: US 8,202,564 B2
(45) Date of Patent: Jun. 19, 2012

(54) METHOD FOR PATTERNING A MEDICAL DEVICE

(75) Inventor: Ahmad R. Hadba, Wallingford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/314,399

(22) Filed: Dec. 8, 2011

(65) Prior Publication Data

US 2012/0073064 A1    Mar. 29, 2012

Related U.S. Application Data

(63) Continuation of application No. 12/160,933, filed as application No. PCT/US2007/004478 on Feb. 22, 2007, now Pat. No. 8,092,856.

(60) Provisional application No. 60/775,767, filed on Feb. 22, 2006.

(51) Int. Cl.
  *B05D 3/00*    (2006.01)

(52) U.S. Cl. ............................................. 427/2.23
(58) Field of Classification Search ............ 427/2.23
  See application file for complete search history.

(56) References Cited

U.S. PATENT DOCUMENTS

| 4,063,878 | A | 12/1977 | Weeks |
| 8,092,856 | B2 * | 1/2012 | Hadba .................. 427/2.23 |
| 2002/0156471 | A1 | 10/2002 | Stern et al. |
| 2004/0131956 | A1 | 7/2004 | Machiguchi et al. |
| 2004/0153125 | A1 | 8/2004 | Roby |
| 2005/0079200 | A1 | 4/2005 | Rathenow et al. |

FOREIGN PATENT DOCUMENTS

JP    10306228  A2    11/1998

OTHER PUBLICATIONS

International Search Report for PCT/US07/004478 date of completion is Nov. 20, 2007 (10 pages).

* cited by examiner

*Primary Examiner* — Peter Szekely

(57) ABSTRACT

The present disclosure provides a method for forming a color pattern on a medical device.

16 Claims, No Drawings

METHOD FOR PATTERNING A MEDICAL DEVICE

CROSS-REFERENCE TO RELATED APPLICATION

This application is a continuation of U.S. application Ser. No. 12/160,933 filed Jul. 15, 2008, now U.S. Pat. No. 8,092,856, which is a National Stage Application of PCT/US2007/004478, filed Feb. 22, 2007, under 35 USC §371(a), which claims priority of U.S. Provisional Patent Application Ser. No. 60/775,767 filed Feb. 22, 2006, the disclosures of each of the above-identified applications are hereby incorporated by reference in their entirety.

BACKGROUND

1. Technical Field

The present disclosure relates to a method for patterning a medical device, and more particularly, a method for color-patterning a dyed medical device, such as a suture.

2. Background of Related Art

It is well known in the art that methods for coloring a medical device, such as a suture, may be utilized to enhance their visibility during laparoscopic procedures. Additionally, colored sutures allow for immediate brand recognition by the personnel that use the suture material, i.e., doctors, nurses, and other surgical team members.

U.S. Pat. No. 4,008,303 discloses a method of coloring polyglycolic acid surgical elements by incorporating 1,4-bis(p-toluidino)-anthraquinone into molten polyglycolic acid to form pellets which may then be spun to form green filaments.

U.S. Pat. No. 5,312,437 discloses a method for forming a dyed braid by dry blending a colorant with a non-absosrbable resin to form a blend and extruding the blend to form filaments which may be braided to form sutures.

Notwithstanding these known methods, it would be advantageous to provide more effective methods for coloring medical devices that not only enhance visibility during surgical procedures but also provide more intricate color-patterns on the medical device.

SUMMARY

Methods are described wherein color-patterns are formed on medical devices. The methods include the steps of applying at least one volatile dye to a medical device, applying at least one masking agent to predetermined portions of the dyed medical device, and treating the masked, dyed medical device to remove the at least one volatile dye to thereby form a colored pattern on the medical device.

DETAILED DESCRIPTION

The present methods can be used to form color patterns on any medial device. The color pattern on the medical device may improve visualization of the device during implantation or use in a patient. Some examples of medical devices which may be treated in accordance with the present disclosure include, but are not limited to, sutures, staples, meshes, patches, slings, stents, grafts, clips, pins, screws, rivets, tacks, bone plates, drug delivery devices, wound dressings, woven devices, non-woven devices, braided devices, adhesion barriers, tissue scaffolds, and other implants.

The medical device can be formed from any material that has suitable physical properties for the intended use of the medical device. Medical devices can thus be formed of absorbable materials, nonabsorbable materials, and combinations thereof. Suitable absorbable materials which may be utilized to form the medical device include trimethylene carbonate, caprolactone, dioxanone, glycolic acid, lactic acid, glycolide, lactide, homopolymers thereof, copolymers thereof, and combinations thereof. Suitable non-absorbable materials which may be utilized to form the medical device include polyolefins, such as polyethylene, polypropylene, copolymers of polyethylene and polypropylene, and blends of polyethylene and polypropylene. In embodiments, the medical device can be sterilized.

In some embodiments, the medical device may be a suture. Suitable absorbable materials which may be utilized for sutures include polyesters such as glycolide, caprolactone, trimethylene carbonate, lactide, and various combinations thereof. Examples of sutures made of such materials include those commercially available and sold under the name POLYSORB®, CAPROSYN®, BIOSYN®, SURGIPRO® and VASCUSIL®.

In some embodiments the medical device may be formed from one or more filaments. Where formed of more than one filament, the filaments can be knitted, braided, woven or non-woven.

The methods for patterning a medical device disclosed herein include the following steps: applying at least one volatile dye to a medical device; applying at least one masking agent to the dyed medical device; and treating the masked, dyed medical device to form a color pattern on the medical device.

A volatile dye may include, for example, any dye, color or pigment capable of being selectively removed from the bulk material of a given medical device when exposed to the treatment processes described herein. Some examples of volatile dyes include, but are not limited to Color Index (C.I.) No. 74160 (copper phthalocyanine, [phthalocyaninato (2-)] copper, also referred to as copper tetrabenzoporphyrazine or tetrabenzo-5,10,15,20-diazaporphyrinephthalocyanine); C.I. No. 61565 (D&C Green No. 6 (principally 1,4-bis[(4-methylphenyl)amino]-9,10-anthracenedione)); C.I. No. 73000 (D&C Blue No. 6 ([Δ-2,2'-biindoline]-3,3'-dione) or 2-(1,3-dihydro-3-oxo-2H-indol-zylidene)-1,2-dihydro-3H-indol-3-on); and C.I. No. 60725 (D&C Violet No. 2 (principally 1-hydroxy-4-[(4-methyphenyl)amino]-9,10-anthracenedione)) or 1,4-hydroxy-1-(p-toluidino)anthroquinone. In embodiments, the dye may be an FDA-approved dye which may be employable in medical devices, including sutures. In one embodiment, the at least one volatile dye may be D&C Violet Number 2.

In addition to at least one volatile dye, the present methods described herein also utilize at least one masking agent in patterning a medical device. The at least one masking agent may include any agent able to prevent or hinder the extraction of the at least one volatile dye from the medical device during the treatment processes described herein. Suitable masking agents include, but are not limited to, metal salts of fatty acids.

Examples of fatty acids useful for forming a metal salt of a fatty acid useful herein includes butyric, caproic, caprylic, capric, lauric, myristic, palmitic, palmitoleic, stearic, oleic, linoleic, linolenic, etc. Examples of monovalent metals useful for forming a metal salt of a fatty acid useful in the various embodiments described herein include lithium, rubidium, cesium, francium, copper, silver and gold. Examples of polyvalent metals useful for forming a metal salt of a fatty acid useful in the various embodiments described herein include calcium, magnesium, beryllium, aluminum, tin, lead, bismuth and the polyvalent transition metals. Some examples of useful masking agents include, but are not limited to, calcium stearate, magnesium stearate, barium stearate, aluminum stearate, zinc stearate, calcium palmitate, magnesium palmitate, barium palmitate, aluminum palmitate, zinc palmitate, calcium oleate, magnesium oleate, barium oleate, aluminum oleate, and zinc oleate. In some embodiments, the at least one masking agent is calcium stearate.

In embodiments the volatile dye and/or the at least one masking agent may be combined with any polymer or other suitable material utilized to form the medical device prior to forming the medical device, thereby incorporating the volatile dye and/or the at least one masking agent into the medical device. For example, a dye may be added to a polymer utilized to form a suture after polymerization, but prior to extrusion. In other embodiments, the at least one masking agent and/or the volatile dye may be applied to the surface of the medical device either simultaneously or sequentially, for example, the dye may first be applied to the surface of the medical device followed by application of the masking agent. Combinations of these treatments may also be used, for example, the volatile dye may be combined with a polymer utilized to form a medical device while the at least one masking agent may be applied as a coating on the dyed medical device.

The at least one masking agent can be applied to the medical device in any amount sufficient to form the desired color pattern. The amount of the at least one masking agent in the dyed medical device may be from about 0.01% to about 10% by weight of the medical device, in embodiments from about 0.1% to about 5%, in other embodiments from about 0.5% to about 2.5% by weight of the medical device.

In embodiments, the masking agent may be combined with any polymer within the purview of those skilled in the art and applied as a coating to the medical device. Suitable polymers include bioabsorbable polymers such as polylactic acid, polyglycolic acid, polydioxanone, polycaprolactone, copolymers of glycolide and trimethylene carbonate, polylactide/polyglycolide copolymers, polyesteramides, trimethylene carbonate, tetramethylene carbonate, dimethyl trimethylene carbonate, dioxanones, dioxepanones, absorbable cyclic amides, absorbable cyclic ether-esters derived from crown ethers, beta hydroxyacids (such as beta hydroxybutyric acid and gamma hydroxyvaleric acid), polyalkyl ethers (such as polyethylene glycol and polypropylene glycol) and combinations thereof.

Where present, the polymer coating may be present in an amount from about 0.3% to about 10% by weight of the medical device, in embodiments from about 0.5% to about 5% by weight of the medical device, in other embodiments from about 0.7% to about 2.5% by weight of the medical device.

In embodiments, the at least one masking agent, and any optional polymer in combination thereof, may be combined with a solvent to form a coating solution or any combination thereof. The order of addition of materials to form such coating solution is not critical and therefore may be determined through routine experimentation depending upon the desired use. Suitable solvents which may be utilized include, for example, alcohols, e.g., methanol, ethanol, and propanol; chlorinated hydrocarbons such as methylene chloride, chloroform, and 1,2-dichloro-ethane; and aliphatic hydrocarbons such as hexane, heptene, and ethyl acetate. When desirable, heat may be applied to the solvent mixture to improve the solubility of the masking agent and any optional polymer. For example, temperatures from about 30° C. to about 60° C. may be utilized in some cases.

It is envisioned that the at least one masking agent, as well as the at least one volatile dye, can be applied to a medical device by any suitable process, e.g. passing the medical device through a solution, or past a brush or other coating solution applicator, or past one or more spray nozzles, or dipped directly into the at least one volatile dye and/or or at least one masking agent.

In embodiments, the at least one masking agent, in combination with an optional coating material, can be applied to the medical device to cover the entire medical device. In other embodiments, the at least one masking agent, in combination with an optional coating material, can be applied partially or intermittently to cover portions of the medical device to form a pattern thereon. It is envisioned that the masking agent and optional coating may be applied to the medical device in any fashion known for creating color patterns on devices, including the use of masks or ink-jet printing.

After applying at least one masking agent to a dyed medical device, the medical device may be treated to form a color pattern on the medical device. Suitable methods of treatment include, for example, heat-treating, increased pressurization, exposure to an inert gas such as nitrogen and combinations thereof. In some embodiments, the treatment process may include a combination of methods, such as heat-treating the masked and dyed medical device under exposure to nitrogen. In other embodiments, the treatment may include heating in a vacuum, which may be at a pressure of from about 50 m torr to about 700 torr.

The masked and dyed medical device may be exposed to a temperature from about 75° C. to about 175° C., in embodiments from about 100° C. to about 150° C. In one embodiment, the masked and dyed medical device may be exposed to a temperature of about 120° C.

It is envisioned that the time and temperature needed to treat the dyed medical device may vary depending upon the size of the medical device, as well as the amount of the at least one volatile dye or the at least one masking agent used to coat the device. Regardless of the treatment utilized, the medical device may be treated from about 10 minutes to about 24 hours, in embodiments from about 15 minutes to about 120 minutes, typically from about 30 minutes to about 60 minutes.

When the masked, dyed medical device is treated, the volatile nature of the dye causes the dye to be removed from the medical device in the areas of the medical device that do not contain the masking agent. These unmasked areas lose color and return to the natural color of the undyed medical device. However, the areas of the medical device that contain the masking agent retain their original color or experience a change in color thereby creating a colored pattern on the treated medical device.

It is further envisioned that the color-patterned medical devices may further contain optional ingredients. Some examples of optional ingredients include, but are not limited to, solvents, bioactive agents, lubricants, emulsifiers, and fragrances. These optional ingredients may represent from about 0.01% to about 20% by weight of the color patterned medical device. In some embodiments, the optional ingredients may represent from about 0.1% to about 10% by weight of the medical device.

The amount of the at least one volatile dye remaining in the dyed medical device after treatment in accordance with the methods of the present disclosure may be from about 0.01% to about 5% by weight of the medical device. In some embodiments from about 0.03% to about 3% by weight of the medical device, typically from about 0.05% to about 1% by weight of the medical device.

In some embodiments, a solvent may be used to remove excess masking agent from the dyed medical device after being treated as described above. Some examples of suitable solvents include, but are not limited to, alcohols, e.g., methanol, ethanol, propanol, chlorinated hydrocarbons (such as methylene chloride, chloroform, 1,2-dichloro-ethane), and aliphatic hydrocarbons.

The following examples are given as an illustration of forming color-patterned medical devices as described herein. It should be noted that the various embodiments described herein are not limited to the specific details embodied in the examples.

EXAMPLE 1

Five different size POLYSORB® braided sutures (sizes 2, 1, 0, 2/0, and 3/0) were dyed with D&C Violet No. 2 and coated with a coating containing a copolymer consisting of 65% lactide and 35% glycolide in combination with calcium stearate. Using three different lots of each of the five different size POLYSORB® braids, suture samples from each braid lot were cut into 6 pieces of approximately 15 inches in length. The samples were treated in a Blue M oven (General Signal Co.) at about 120° C. under the flow of nitrogen for a period of time from about 10 minutes to about 24 hours. The sutures were visibly analyzed every 15 minutes over the first 60 minutes and then again after 120 minutes. The treated sutures were rated based upon color and spottiness. The summary of the results are shown in Table 1 below.

TABLE 1

| Sample Name | Size | Coating Level | App | ninh | Spot | 15 min | 30 min | 45 min | 60 min | 120 min |
|---|---|---|---|---|---|---|---|---|---|---|
| 330NH 018-3/0-02 | 3/0 | 6.39 | V | 1.3 | 3 | FS | FS | N; SB | N; SB | B; SBL |
| 330NH 019-3/0-05 | 3/0 | 5.67 | V | 1.3 | 3 | S | FS | FS; SB | N; SB | B; G |
| 330NH 019-3/0-07 | 3/0 | 4.72 | V | 1.3 | 1 | S | FS | SB | SB | B; BL |
| 330NH 022-2/0-08 | 2/0 | 3.44 | DC | 1.3 | 2 | S | S | FS | SBL | BL |
| 330NH 008-0-5 | 0 | 2.95 | V | 1.04 |  | N | N | N | SB | B; G |
| ARH346NH 083-02-OV | 0 | 1.24 | C | 1.04 |  | N | N | N | F; SB | B |
| 330NH 6-1-10-03A | 1 | 1.58 | C | 1.04 |  | S | FS | N; SG | SB | B |
| 330NH 1-2-10-02B | 2 | 0.9 | C | 1.04 |  | S | S | N | SB | B |
| 330NH 1-2-06A | 2 | 1.12 | C | 1.04 |  | S | FS | FS | SB | B |

Code
N = No visible spots
S = Spotty
B = Braid Blue in color
G = Grey color
BL = Bleaching (lighter blue)
FS = Few visible spots
VFS = Very few visible spots
VS = Very spotty
SB = Start to blue in color
SBL = Start to bleach (lighter blue color)

As shown in Table 1, as the time of treatment increased, the sutures started to bleach and return to their natural color in those areas lacking the masking agent, with a blue color becoming prevalent in the areas where the masking agent had been applied. Most braids were not of uniform color after approximately 15 minutes. It was observed that the color of the braid changed as the time of treatment increased. The areas that had heavier deposits of calcium stearate, originally identified as white spots or streaking, became bluish in color, while the areas without the heavier deposits of calcium stearate returned to the natural color of the undyed suture braids.

It was also observed that bleaching and color change correlated with the braid size, i.e., smaller size braids lost color faster than larger braids. Also, braids coated with a higher level of calcium stearate appeared to bleach or change color at a slower rate than the uncoated or braids with less coating. Overall, most white streaks disappeared and the strongest blue color was obtained, especially for smaller sutures, after about 30 minutes to about 60 minutes of heating.

It will be understood that various modifications may be made to the embodiments disclosed herein. Therefore, the above description should not be construed as limiting, but merely as exemplifications of useful embodiments. Those skilled in the art will envision other modifications within the scope and spirit of the claims appended hereto.

What is claimed is:

1. A method for color-patterning a medical device comprising:
    forming a medical device from a combination of materials comprising at least one volatile dye and at least one polymer;
    applying at least one masking agent to predetermined portions of the formed medical device to provide masked and unmasked portions of the medical device; and
    treating the medical device to remove the at least one volatile dye from the unmasked portion of the medical device thereby forming a color pattern on the medical device.

2. The method of claim 1 wherein the formed medical device comprises a medical device selected from the group consisting of a suture, staple, mesh, patch, sling, stent, graft, clip, pin, screw, rivet, tack, bone plate, drug delivery device, wound dressing, woven device, non-woven device, braided device, adhesion barrier, and tissue scaffold.

3. The method of claim 1 wherein the medical device is a suture.

4. The method of claim 1 wherein the at least one volatile dye is selected from the group consisting of copper phthalocyanine, D&C Green No. 6, D&C Blue No. 6, D&C Violet No. 2, and combinations thereof.

5. The method of claim 1 wherein the at least one volatile dye comprises D&C Violet No. 2.

6. The method of claim 1 wherein the at least one polymer comprises an absorbable polymer.

7. The method of claim 1 wherein the at least one polymer comprises a non-absorbable polymer.

8. The method of claim 1 wherein forming the medical device comprises extrusion.

9. The method of claim 1 wherein the at least one masking agent comprises a metal salt of a fatty acid.

10. The method of claim 1 wherein the at least one masking agent comprises an agent selected from the group consisting of calcium stearate, magnesium stearate, barium stearate, aluminum stearate, zinc stearate, calcium palmitate, magnesium palmitate, barium palmitate, aluminum palmitate, zinc palmitate, calcium oleate, magnesium oleate, barium oleate, aluminum oleate, zinc oleate, and combinations thereof.

11. The method of claim 1 wherein the at least one masking agent comprises calcium stearate.

12. The method of claim 1 wherein the at least one masking agent further comprises a bioabsorbable polymer in combination with the at least one masking agent.

13. The method of claim 1 wherein the at least one masking agent further comprises a non-bioabsorbable polymer in combination with the at least one masking agent.

14. The method of claim 1 wherein treating the medical device comprises exposing the medical device to a temperature from about 75° C. to about 175° C.

15. The method of claim 1 wherein treating the medical device further comprises exposing the medical device to a pressure of from about 50 m torr to about 700 torr.

16. The method of claim 1 wherein treating the medical device comprises treating the medical device from about 10 minutes to about 24 hours.

* * * * *